(12) United States Patent
Gershuni et al.

(10) Patent No.: US 11,607,323 B2
(45) Date of Patent: Mar. 21, 2023

(54) PATELLOFEMORAL TRIAL EXTRACTOR

(71) Applicant: Howmedica Osteonics Corp., Mahwah, NJ (US)

(72) Inventors: Vladimir Gershuni, Brooklyn, NY (US); Kristen Shaughnessy, Ridgewood, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 637 days.

(21) Appl. No.: 16/598,346

(22) Filed: Oct. 10, 2019

(65) Prior Publication Data

US 2020/0113710 A1 Apr. 16, 2020

Related U.S. Application Data (60) Provisional application No. 62/745,593, filed on Oct. 15, 2018.

(51) Int. Cl.
| | | |
|---|---|---|
| *A61F 2/46* | (2006.01) | |
| *A61B 17/88* | (2006.01) | |
| *A61B 17/00* | (2006.01) | |

(52) U.S. Cl.
CPC .............. *A61F 2/461* (2013.01); *A61B 17/88* (2013.01); *A61B 2017/0042* (2013.01)

(58) Field of Classification Search
CPC .. A61F 2/4611; A61F 2/46; A61F 2002/4619; A61F 2/461
See application file for complete search history.

(56) References Cited

U.S. PATENT DOCUMENTS

| | | |
|---|---|---|
| 3,857,989 A | 12/1974 | King |
| 4,009,712 A | 3/1977 | Burstein et al. |
| 4,222,382 A | 9/1980 | Antonsson et al. |
| 4,399,813 A | 8/1983 | Barber |
| 4,406,023 A | 9/1983 | Harris |
| 4,421,507 A | 12/1983 | Bokros |
| 4,459,985 A | 7/1984 | McKay et al. |
| 4,498,468 A | 2/1985 | Hansson |
| 4,514,865 A | 5/1985 | Harris |
| 4,798,213 A | 1/1989 | Doppelt |
| 4,888,023 A | 12/1989 | Averill et al. |
| 4,936,313 A | 6/1990 | Burkhardt et al. |
| D309,778 S | 8/1990 | Torre |
| 4,965,458 A | 10/1990 | Jeng et al. |

(Continued)

*Primary Examiner* — Andrew Yang
(74) *Attorney, Agent, or Firm* — Lerner, David, Littenberg, Krumholz & Mentlik, LLP (57) ABSTRACT

Disclosed herein are insertion and extraction instruments for orthopaedic procedures that are used for inserting and extracting trials and implants. The instruments include a body extending along a central axis having first and second arms extending from the body along first and second axes. The first and second arms may be moveable with the distal ends of the arms being configured to engage first and second engagement feature of a trial or an implant. The first and second axes define an angle therebetween such that when the distal end of the first arm is received in a first engagement feature of the implant and the distal end of the second arm is in the second engagement feature, the distal ends of the arms are urged against respective first and second side walls of the first and second arms to secure the instrument to the trial or implant.

19 Claims, 10 Drawing Sheets

(56) References Cited

U.S. PATENT DOCUMENTS

| | | | |
|---|---|---|---|
| 4,983,162 A | 1/1991 | Metais et al. |
| 4,997,434 A | 3/1991 | Seedhom et al. |
| 5,049,150 A | 9/1991 | Cozad |
| D320,451 S | 10/1991 | Torre |
| 5,417,693 A | 5/1995 | Sowden et al. |
| 5,425,775 A | 6/1995 | Kovacevic et al. |
| 5,609,595 A | 3/1997 | Pennig |
| 5,697,932 A | 12/1997 | Smith et al. |
| 5,702,476 A | 12/1997 | Limacher et al. |
| 5,704,788 A | 1/1998 | Milne |
| 5,749,878 A | 5/1998 | Bracy et al. |
| 5,859,437 A | 1/1999 | Hsu et al. |
| 5,868,711 A | 2/1999 | Kramer et al. |
| 5,899,920 A | 5/1999 | DeSatnick et al. |
| 5,937,530 A | 8/1999 | Masson |
| 6,063,091 A | 5/2000 | Lombardo et al. |
| 6,063,124 A | 5/2000 | Amstutz |
| 6,102,849 A | 8/2000 | Hakac |
| 6,264,657 B1 | 7/2001 | Urbahns et al. |
| 6,267,025 B1 | 7/2001 | Sand et al. |
| 6,309,395 B1 | 7/2001 | Sand et al. |
| 6,416,484 B1 | 7/2002 | Miller et al. |
| 6,638,902 B2 | 10/2003 | Tarara et al. |
| 6,709,460 B2 | 3/2004 | Merchant |
| 6,731,769 B1 | 5/2004 | Lenhardt |
| 6,733,504 B2 * | 5/2004 | Lin ........................ A61F 2/446 |
| | | 606/247 |
| 6,746,487 B2 | 6/2004 | Scifert et al. |
| 7,097,648 B1 | 8/2006 | Globerman et al. |
| 7,101,181 B2 | 9/2006 | Bompard et al. |
| 7,115,131 B2 | 10/2006 | Engh et al. |
| 7,225,027 B2 | 5/2007 | Zeng et al. |
| 7,258,701 B2 | 8/2007 | Aram et al. |
| 7,491,205 B1 | 2/2009 | Michelson |
| 7,520,901 B2 | 4/2009 | Engh et al. |
| 7,539,332 B1 | 5/2009 | Al-Dayeh et al. |
| 7,662,156 B2 | 2/2010 | Carson |
| 7,766,917 B2 | 8/2010 | Kugler et al. |
| 7,896,884 B2 | 3/2011 | Wing et al. |
| 7,896,922 B2 | 3/2011 | Engh et al. |
| 7,935,151 B2 | 5/2011 | Haines |
| 8,002,840 B2 | 8/2011 | Aram et al. |
| 8,021,368 B2 | 9/2011 | Haines |
| 8,062,377 B2 | 11/2011 | Haines |
| 8,078,440 B2 | 11/2011 | Haines |
| 8,088,167 B2 | 1/2012 | Haines |
| 8,152,855 B2 | 4/2012 | Tulkis et al. |
| 8,273,111 B2 | 9/2012 | Amato et al. |
| 8,298,241 B2 | 10/2012 | Arnhold |
| D679,012 S | 3/2013 | Gleixner et al. |
| D679,394 S | 4/2013 | Gleixner et al. |
| 8,430,932 B2 | 4/2013 | Haines |
| 8,437,844 B2 | 5/2013 | Syed Momen et al. |
| 8,454,621 B2 | 6/2013 | DeRidder et al. |
| 8,475,535 B2 | 7/2013 | Otto |
| 8,500,816 B2 | 8/2013 | Dees, Jr. et al. |
| 8,535,383 B2 | 9/2013 | Aram et al. |
| 8,551,101 B2 | 10/2013 | Kuczynski |
| 8,577,473 B2 | 11/2013 | Schleich et al. |
| 8,591,298 B1 | 11/2013 | Watson et al. |
| 8,617,085 B2 | 12/2013 | Moran, Jr. |
| 8,679,167 B2 | 3/2014 | Tipirneni et al. |
| 8,894,475 B2 | 11/2014 | Breiland |
| 8,920,427 B2 | 12/2014 | Major et al. |
| 8,948,877 B2 | 2/2015 | Schleich et al. |
| 9,055,976 B2 | 6/2015 | Li |
| 9,125,617 B2 | 9/2015 | Lee |
| 9,138,241 B2 | 9/2015 | Kuczynski |
| 9,162,008 B2 | 10/2015 | Serafin, Jr. et al. |
| 9,173,745 B2 | 11/2015 | Dinville et al. |
| 9,226,829 B2 | 1/2016 | Bartels et al. |
| 9,259,508 B2 | 2/2016 | Serafin, Jr. et al. |
| 9,320,681 B2 | 4/2016 | Dos Santos et al. |
| 9,474,539 B2 | 10/2016 | Catanzarite et al. |
| 9,532,845 B1 | 1/2017 | Dossett et al. |
| 9,649,406 B2 | 5/2017 | Serafin, Jr. et al. |
| 9,655,727 B2 | 5/2017 | Wellings et al. |
| 9,675,367 B2 | 6/2017 | Murray et al. |
| 9,694,102 B2 | 7/2017 | Serafin, Jr. et al. |
| 9,700,330 B2 | 7/2017 | Wyant et al. |
| 9,706,970 B2 | 7/2017 | Monga et al. |
| 9,770,279 B2 | 9/2017 | Kellar et al. |
| 9,808,348 B2 | 11/2017 | Dees, Jr. et al. |
| 9,833,542 B2 | 12/2017 | Serafin, Jr. et al. |
| 9,888,328 B2 | 2/2018 | Zhong et al. |
| 2001/0001121 A1 | 5/2001 | Lombardo et al. |
| 2003/0088253 A1 | 5/2003 | Seil |
| 2003/0171816 A1 | 9/2003 | Scifert et al. |
| 2004/0153091 A1 | 8/2004 | Figueroa et al. |
| 2004/0167630 A1 | 8/2004 | Rolston |
| 2005/0069835 A1 | 3/2005 | Bompard et al. |
| 2005/0246028 A1 | 11/2005 | Pappas et al. |
| 2005/0267584 A1 | 12/2005 | Burdulis et al. |
| 2006/0030134 A1 | 2/2006 | Kim et al. |
| 2006/0047296 A1 | 3/2006 | Embry et al. |
| 2006/0116680 A1 | 6/2006 | Kugler et al. |
| 2006/0121415 A1 | 6/2006 | Anitua Aldecoa |
| 2006/0200162 A1 | 9/2006 | Farling et al. |
| 2007/0037123 A1 | 2/2007 | Mansueto et al. |
| 2007/0162026 A1 | 7/2007 | Tipirneni et al. |
| 2008/0045969 A1 | 2/2008 | Kugler et al. |
| 2008/0058668 A1 | 3/2008 | Seyed Momen et al. |
| 2008/0058949 A1 | 3/2008 | Dees et al. |
| 2008/0097435 A1 | 4/2008 | DeRidder et al. |
| 2008/0097454 A1 | 4/2008 | DeRidder et al. |
| 2008/0097526 A1 | 4/2008 | Accardo |
| 2008/0109085 A1 | 5/2008 | Tulkis et al. |
| 2008/0147126 A1 | 6/2008 | Tipirneni et al. |
| 2008/0171951 A1 | 7/2008 | Fell |
| 2008/0177275 A1 | 7/2008 | Wing et al. |
| 2009/0062808 A1 | 3/2009 | Wolf, II |
| 2009/0112219 A1 | 4/2009 | Daniels et al. |
| 2009/0112365 A1 | 4/2009 | Orr et al. |
| 2009/0131936 A1 | 5/2009 | Tipirneni et al. |
| 2009/0157143 A1 | 6/2009 | Edler et al. |
| 2009/0209968 A1 | 8/2009 | Copf, Jr. |
| 2009/0240254 A1 | 9/2009 | Arnhold |
| 2009/0299370 A1 | 12/2009 | Kiester |
| 2009/0299415 A1 | 12/2009 | Pimenta |
| 2009/0312819 A1 | 12/2009 | Klefenz et al. |
| 2009/0326543 A1 | 12/2009 | Fabian, Jr. |
| 2010/0004691 A1 | 1/2010 | Amato et al. |
| 2010/0069786 A1 | 3/2010 | Globerman et al. |
| 2010/0222887 A1 | 9/2010 | Katrana et al. |
| 2010/0241237 A1 | 9/2010 | Pappas |
| 2010/0280624 A1 | 11/2010 | Engh et al. |
| 2010/0293115 A1 | 11/2010 | Seyed Momen |
| 2011/0004274 A1 | 1/2011 | Schleich et al. |
| 2011/0004318 A1 | 1/2011 | Tulkis et al. |
| 2011/0083566 A1 | 4/2011 | Backus |
| 2011/0097688 A1 | 4/2011 | Rebaudi |
| 2011/0189634 A1 | 8/2011 | Kfir |
| 2011/0202063 A1 | 8/2011 | Bonnin et al. |
| 2011/0288438 A1 | 11/2011 | Lee |
| 2011/0305806 A1 | 12/2011 | Ventimiglia |
| 2011/0319003 A1 | 12/2011 | Breiland |
| 2012/0116466 A1 | 5/2012 | Dinville et al. |
| 2012/0116519 A1 | 5/2012 | Copf, Jr. |
| 2012/0239035 A1 | 9/2012 | Li |
| 2012/0296428 A1 | 11/2012 | Donner |
| 2012/0323334 A1 | 12/2012 | Jones et al. |
| 2013/0045459 A1 | 2/2013 | Vale |
| 2013/0245777 A1 | 9/2013 | Jerry |
| 2013/0282018 A1 | 10/2013 | Deridder et al. |
| 2013/0292292 A1 | 11/2013 | Dos Santos et al. |
| 2013/0343521 A1 | 12/2013 | Lee |
| 2014/0005746 A1 | 1/2014 | Schleich et al. |
| 2014/0148913 A1 | 5/2014 | Bartels et al. |
| 2015/0031992 A1 | 1/2015 | Monga et al. |
| 2015/0125558 A1 | 5/2015 | Hong |
| 2015/0134010 A1 | 5/2015 | Zlotolow |
| 2015/0150549 A1 | 6/2015 | Hirszowicz et al. |
| 2015/0156595 A1 | 6/2015 | Zhong et al. |
| 2015/0327794 A1 | 11/2015 | Rahman et al. |

(56) References Cited

U.S. PATENT DOCUMENTS

| | | |
|---|---|---|
| 2015/0342550 A1 | 12/2015 | Lee |
| 2015/0374499 A1 | 12/2015 | Angeli |
| 2016/0051380 A1 | 2/2016 | Dinville et al. |
| 2016/0074167 A1 | 3/2016 | Vautrin |
| 2016/0166407 A1 | 6/2016 | Mackenzie |
| 2016/0278794 A1 | 9/2016 | Boldt et al. |
| 2016/0331853 A1 | 11/2016 | Taub |
| 2016/0338751 A1 | 11/2016 | Kellar et al. |
| 2017/0007268 A1 | 1/2017 | Catanzarite et al. |
| 2017/0009337 A1 | 1/2017 | Bluck et al. |
| 2017/0020590 A1 | 1/2017 | Faccioli et al. |
| 2017/0172749 A1 | 6/2017 | Wellings et al. |
| 2017/0209242 A1 | 7/2017 | Kukunas et al. |
| 2017/0231552 A1 | 8/2017 | Oosthuizen |
| 2017/0323443 A1 | 11/2017 | Dhruwdas |
| 2018/0028249 A1 | 2/2018 | Jaumard |
| 2018/0042734 A1 | 2/2018 | Slater |
| 2018/0042735 A1 | 2/2018 | Schell et al. |

\* cited by examiner

FIG. 12A

PATELLOFEMORAL TRIAL EXTRACTOR

CROSS-REFERENCE TO RELATED APPLICATIONS

This application claims the benefit of the filing date of U.S. Provisional Patent Application No. 62/745,593 filed on Oct. 15, 2018, the disclosure of which is hereby incorporated herein by reference

FIELD OF INVENTION

The present invention relates generally to insertion and extraction devices for use in orthopaedic procedures including use with trial or prosthesis implanting and extracting.

BACKGROUND OF THE INVENTION

During an orthopaedic replacement procedure, a surgeon may use a trial to assess the placement and size of a prosthesis prior to implantation. In some procedures, the trial needs to be adjusted for fit and easily inserted and removed from the implant site. Various extractors may be used for pulling, manipulating and inserting the trial of an implant or the final implant into the implant site. Such extractors can also be used for removing a trial of an implant or the implant itself from cemented or cementless applications. Current solutions often implement osteotomy or other cutting methods to remove trials. In such solutions there is a risk of damaging the bone periphery, the soft tissues and the bone implant site.

The connection between the extractor and the implant in many such systems is often achieved through cumbersome and time consuming means that do not effectively and easily engage the extractor and quickly remove the implant. For example, many extractors are threaded directly onto the trial. While there is time involved in threading and unthreading the extractor to the trial, at times, the threaded rod of the extractor can fail due to shear loads requiring the shared rod to be drilled out.

As such, an inserter or extractor for aiding in implanting or removing a trial or implant from the bone should have a quick and effective connecting means, and is strong enough to reduce the likelihood of failure, preferably having more than one connection point.

BRIEF SUMMARY OF THE INVENTION

A first aspect of the invention is insertion and extraction instruments for orthopaedic procedures that are used for inserting and extracting trials and implants. The instruments include a body extending along a central axis and first and second arms extending from the body along first and second axes transverse to the central axis. One of the first and second arms is moveable from a first position to a second position along the second axis with distal ends of the arms being configured to engage first and second engagement features of a trial or an implant. The first and second axes define an angle therebetween such that when the distal end of the first arm is received in a first engagement feature of the implant and the distal end of the second arm is in the second engagement feature, the distal ends of the arms are urged against respective first and second side walls of the first and second arms to secure the instrument to the trial or implant.

Another aspect of the invention is an instrument having a body extending along a central axis and first and second arms extending distally from a distal portion of the body along first and second axes respectively, the first and second axes being transverse to the central axis. The first and second arms having first and second distal ends respectively, the second distal end being moveable from a first position to a second position along the second axis, the distal ends configured to engage first and second engagement features of an implant, the first and second engagement features having first and second side walls respectively. The first and second axes define a first angle therebetween such that when the first distal end is received in a first engagement feature of the implant and the second distal end is in the second position, the second end is received in a second engagement feature of the implant such that the first and second distal ends are urged against the first and second side walls respectively to secure the instrument to the implant.

In one embodiment of the second aspect, the first distal end is received in the first engagement feature and the second distal end is in the first position, the instrument can be disengaged from the implant.

In another embodiment of the second aspect, the first and second distal ends have first and second dimensions respectively and the first and second engagement features have first and second engagement feature dimensions respectively, the first and second engagement feature dimensions being greater than the first and second dimensions respectively such that a non-rigid connection is formed between the instrument and the implant when the instrument is secured to the implant to allow movement of the instrument relative to the implant.

In yet another embodiment of the second aspect, the second arm includes a biasing element to urge the second distal end to the second position. The second distal end is a moveable boss disposed in the second arm. A proximal end of the second arm includes a handle to pull the moveable boss from the second position to the first position. The biasing element is a spring disposed around the boss.

In still yet another embodiment of the second aspect, a distal surface extending between the first and second arm is contoured.

In still yet another embodiment of the second aspect, the body includes a grip to hold the instrument. The engagement features may be any of a recess, aperture, side wall, setback and groove.

A third aspect of the invention is an orthopaedic system including an instrument and an implant. The instrument has a body extending along a central axis, first and second arms extending distally from a distal portion of the body along first and second axes respectively, the first and second axes being transverse to the central axis, the first and second arms having first and second distal ends respectively, the second distal end being moveable from a first position to a second position along the second axis. The implant has first and second engagement features configured to receive the first and second distal ends respectively, the first and second engagement features having first and second side walls respectively. The first and second arms define a first angle; the first and second engagement features define a second angle, the first and second angles being equal such that first and second ends are urged against the first and second side walls respectively to secure the instrument to the implant.

A fourth aspect of the invention is a method for engaging or disengaging an implant extractor to a first and a second engagement feature of the implant, the extractor having a body extending along a central axis, first and second arms extending distally from a distal portion of the body along first and second axes respectively, the first and second axes being transverse to the central axis, the first and second arms having first and second distal ends respectively, the second distal end being moveable from a first position to a second position along the second axis. The method comprises engaging the first arm into one of the two engagement features, pushing the body onto the implant such that the second arm is engaged with the second engagement feature, the second arm having a movable boss, and extracting the implant by pulling in a distal to proximal direction.

BRIEF DESCRIPTION OF THE DRAWINGS

A more complete appreciation of the subject matter of the present invention and the various advantages thereof may be realized by reference to the following detailed description, in which reference is made to the following accompanying drawings.

DETAILED DESCRIPTION

Reference will now be made in detail to the various embodiments of the present disclosure illustrated in the accompanying drawings. Wherever possible, the same or like reference numbers will be used throughout the drawings to refer to the same or like features. It should be noted that the drawings are in simplified form and are not drawn to precise scale. Additionally, the term "a," as used in the specification, means "at least one." The terminology includes the words above specifically mentioned, derivatives thereof, and words of similar import. Although at least two variations are described herein, other variations may include aspects described herein combined in any suitable manner having combinations of all or some of the aspects described. As used herein, the terms "implant" and "trial" will be used interchangeably and as such, unless otherwise stated, the explicit use of either term is inclusive of the other term. Similarly, the terms "implant extractor" and "trial extractor" will be used interchangeably and as such, unless otherwise stated, the explicit use of either term is inclusive of the other term.

In describing preferred embodiments of the disclosure, reference will be made to directional nomenclature used in describing the human body. It is noted that this nomenclature is used only for convenience and that it is not intended to be limiting with respect to the scope of the invention. For example, as used herein, the term "distal" means toward the human body and/or away from the operator, and the term "proximal" means away from the human body and/or towards the operator.

Figure 1:
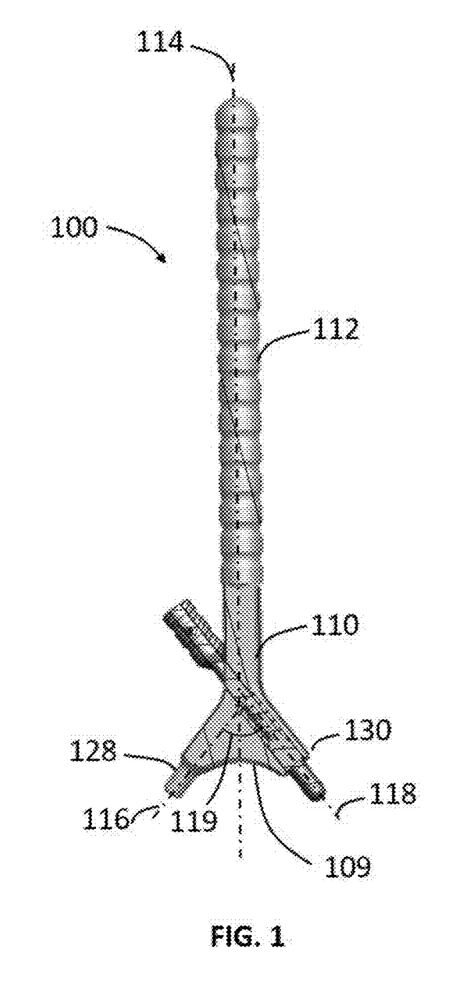
FIG. 1 is a front view of an implant extractor, according to one embodiment of the present disclosure.

Referring to FIG. 1, there is shown an implant extractor 100 according to one embodiment of the present disclosure. Implant extractor 100 includes a first arm 128, a second arm 130, and a body 110 extending along a central axis 114, the body 110 having a grip 112 and a distal portion 108. In other embodiments, the grip 110 may have a ribbed feature for allowing a tighter grip of a user's hand onto the instrument. The first arm 128 and second arm 130 extend from the distal portion 108 of the body 110 along a first axis 116 and second axis 118 respectively. The first and second axes 116, 118 are transverse to the central axis 114. The first and second axes 116, 118 define a first angle 119 which is preferably less than 180 degrees. A distal surface 109 of the distal portion 108 between the first and second arms 128, 130 may be a contoured.

Figure 2:
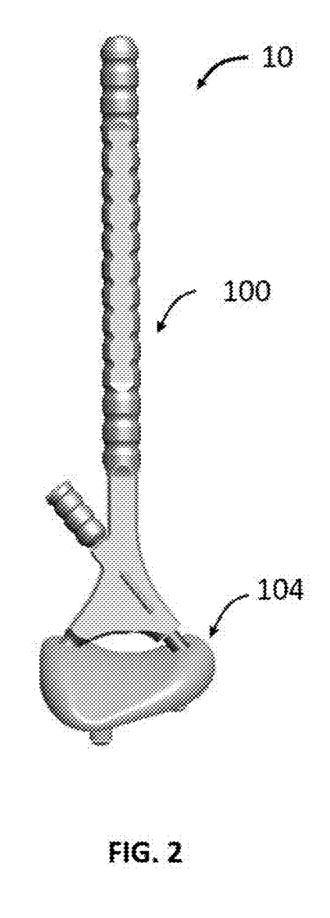
FIG. 2 is a front prospective view of a patellofemoral trial and extractor system having the implant extractor of FIG. 1 engaged with a patellofemoral trial, according to one embodiment of the present disclosure.
Figure 3:
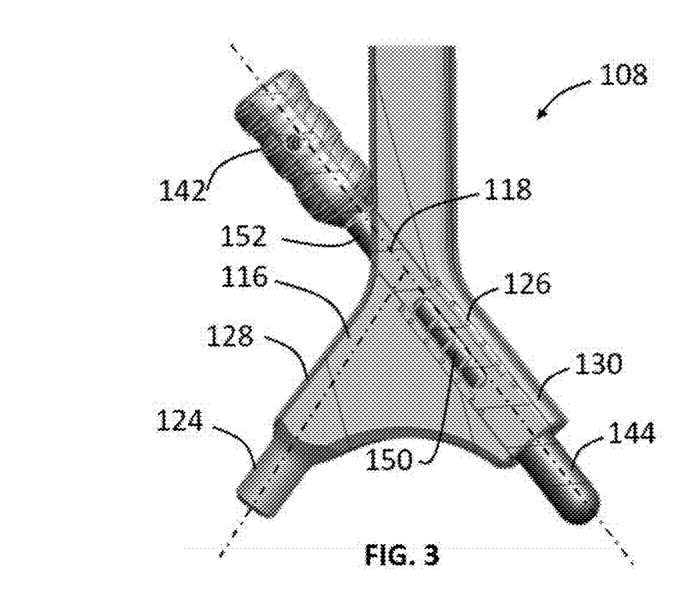
FIG. 3 is a front view of a distal portion of the implant extractor of FIG. 1.

Referring to FIG. 2, there is shown a patellofemoral trial and extractor system 10 having the implant extractor 100 engaged with a patellofemoral trial 104, according to one embodiment of the present disclosure. As shown in FIG. 3, the first and second arms 128, 130 have a first distal end 124 and a second distal end 144 respectively, the second distal end 144 being movable from a first position 200 to a second position 202, discussed in further detail below, and shown in FIG. 10A, for example. The first and second distal ends 124, 144 of the extractor 100 are received in a first aperture 184 and a second aperture 186 of the trial 104. Other embodiments of the patellofemoral trial and extractor system 102 may include implant extractors 100 configured to engage to other implants or trials in the body, including for example, but not by way of limitation, to an acetabular component in total hip replacement procedures.

Figure 4:
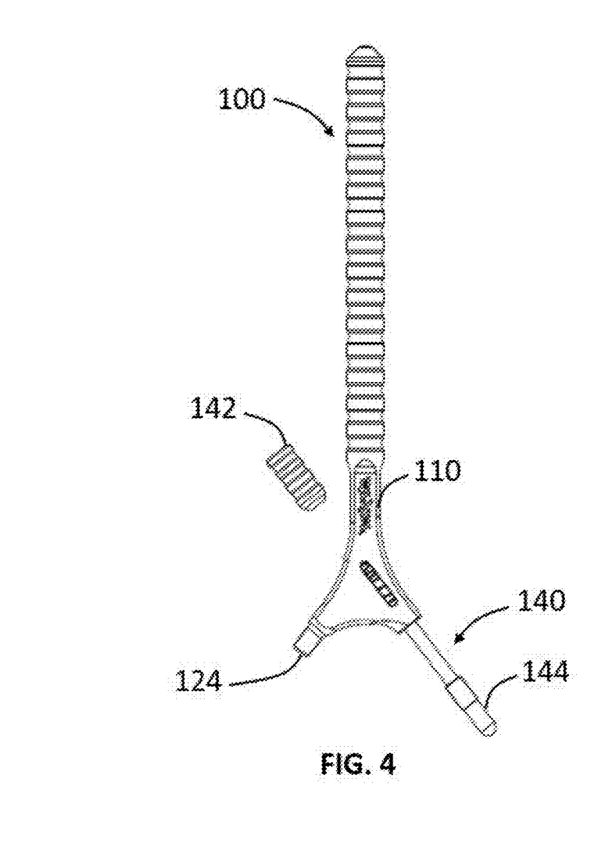
FIG. 4 is an exploded front view of the implant extractor of FIG. 1.

FIGS. 3 and 4 show an assembled view and an exploded view of the implant extractor 100 respectively, with focus on the second arm 130. In FIG. 3, the second arm 130 is in the second position 202. In the shown embodiment, the second distal end 144 may be a moveable boss 140 disposed in the second arm 130, the second arm 130 having a channel 126 in which the moveable boss 140 travels from the first position 200 to the second position 202.

Figure 5:
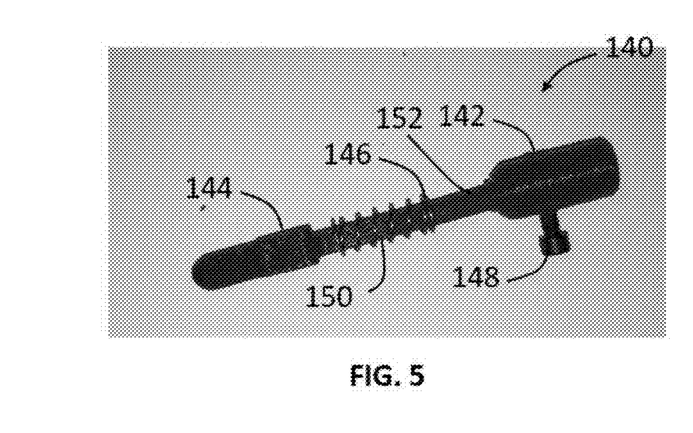
FIG. 5 is side perspective view of a movable boss of the second arm of the implant extractor of FIG. 1.

As shown in FIGS. 4 and 5, a handle 142 may be attached to a proximal end 152 of the movable boss 140 by a retaining screw 148. The handle 142 is utilized to pull the moveable boss 140 from the second position 200 to a first position 202. The second arm 130 may further include a biasing element 146 which urges the second distal end 144 to the second position. 200. The biasing element 146 shown here is a spring disposed around a shaft 150 of the movable boss 140. While a retaining screw is used to attach handle 142 to moveable boss 140 in this embodiment, other embodiments may have other attachments means to attach the moveable boss to the handle. For example, threads, adhesives or welding can be utilized to secure the handle to the moveable boss.

Figure 6A:
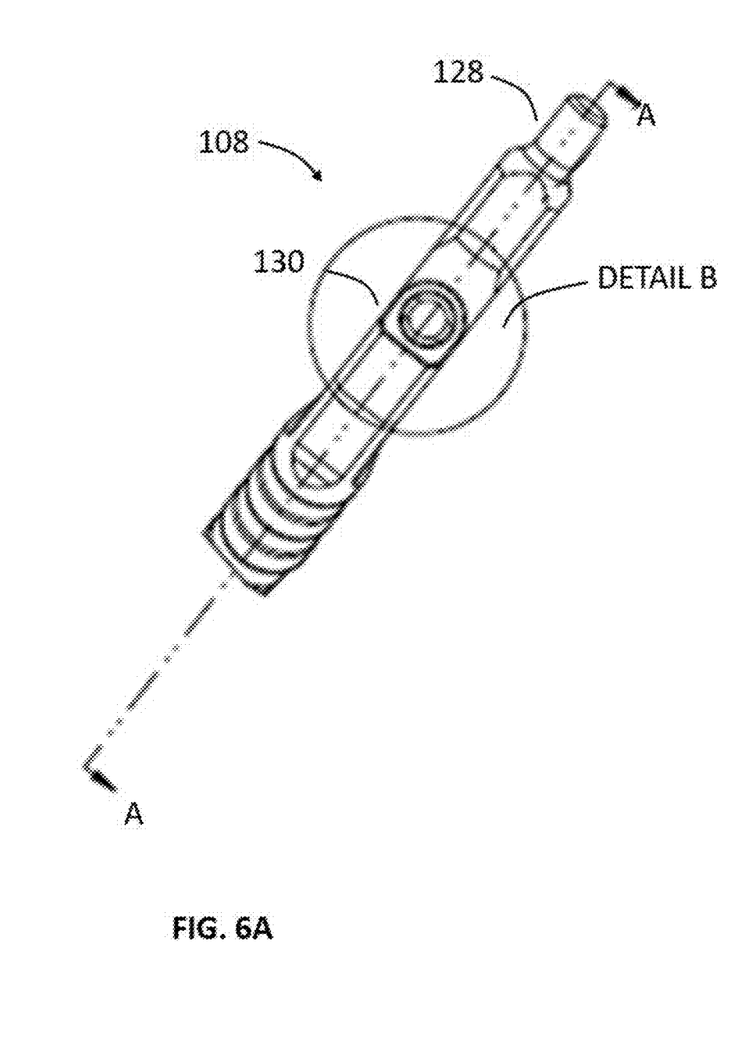
FIG. 6A is a side view of the distal portion of the implant extractor of FIG. 1.
Figure 6B:
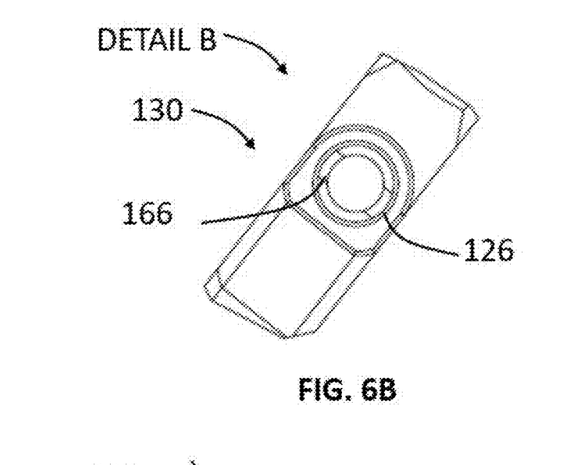
FIG. 6B is a detailed side view of a channel of the implant extractor of FIG. 1.
Figure 6C:
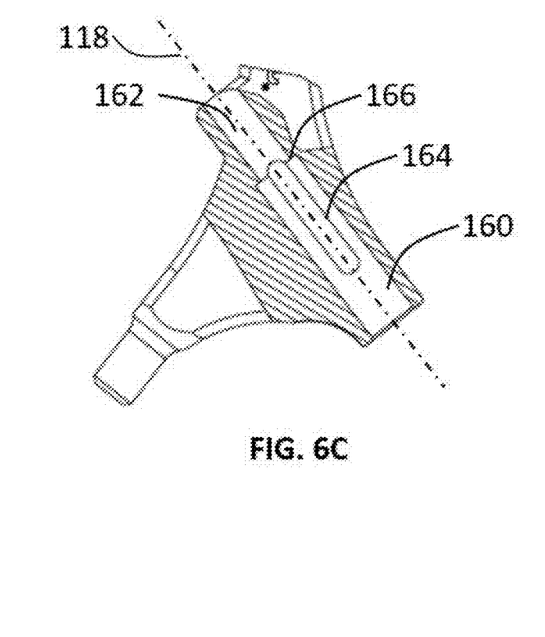
FIG. 6C is a cross-sectional view along line A-A of the distal portion of the implant extractor of FIG. 1

FIG. 6A shows a side view of the distal portion 108, with a Detail B focusing on the channel 126. As shown in FIGS. 6B and 6C, the channel 126 in which the moveable boss 140 travels through has a first aperture 160 along the second axis 118, a second aperture 162 along the second axis 118, and an inner surface 166. The first aperture 160 is wider than the second aperture 162. The first aperture is towards the distal end of the distal portion 108 and extends until the inner surface 166. The second aperture 162 extends from the inner surface 166 therethrough. At the first position 202 the spring 146 (not shown) is at least partially compressed against the inner surface 166. Further, in the shown embodiment, a cut-out 164 extends at least partially along the second axis 118 for purposes of viewing and cleaning the inner components.

Figure 7:
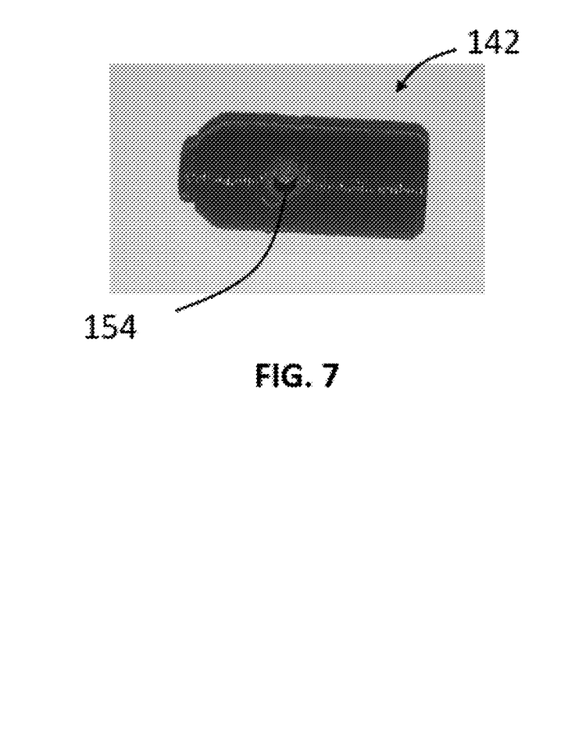
FIG. 7 is a side perspective view of a handle of the second arm of the implant extractor of FIG. 1.
Figure 8A:
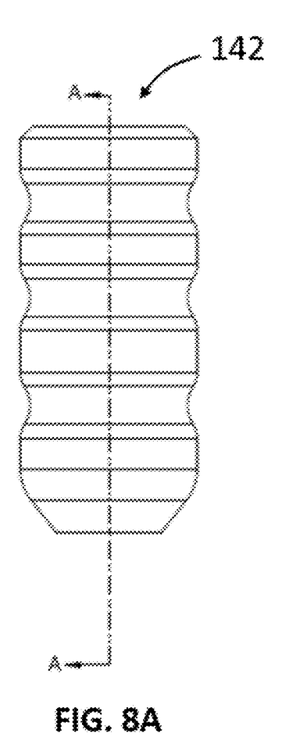
FIGS. 8A and 8B show a side view and a side cross-sectional view along line A-A of a handle of a second arm of an implant extractor according to another embodiment of the present disclosure.
Figure 8B:
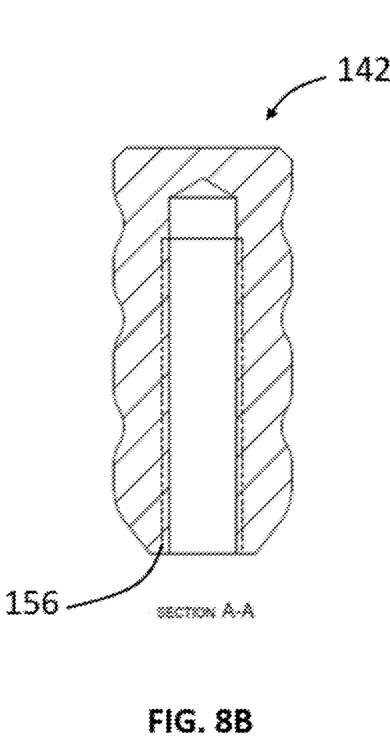

FIG. 7 shows the handle 142 having a threaded retaining screw hole 154 through which the retaining screw 148 is passed through, securing the handle 142 to the shaft 150 of the movable boss 140, the shaft 150 having a corresponding hole (not shown) as to allow passage of the retaining screw 148. In another embodiment, as shown in FIGS. 8A and 8B, the shaft 150 may be press-fit into the interference section 156 of handle 142, securing the shaft 150 to the handle 142.

Figure 9A:
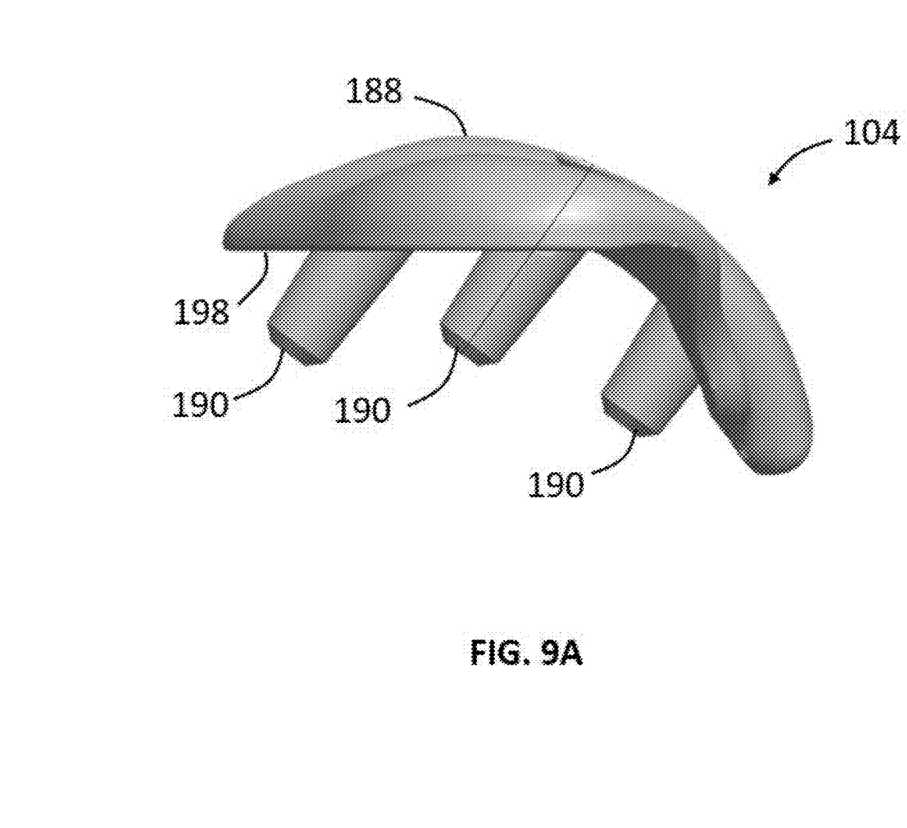
FIGS. 9A-9C show side, front and top perspective views of the patellofemoral trial of FIG. 2A.
Figure 9B:
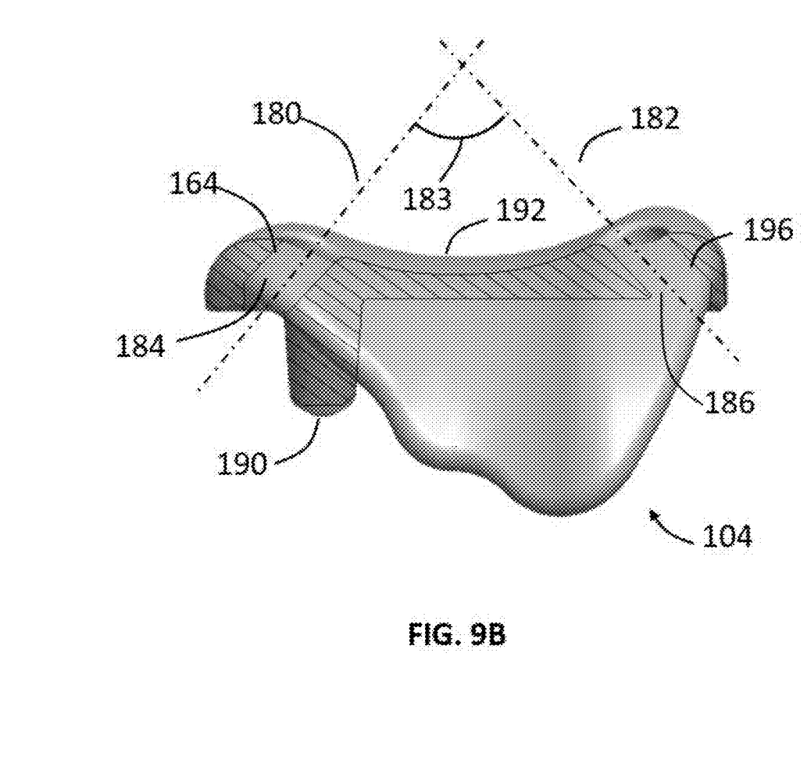
Figure 9C:
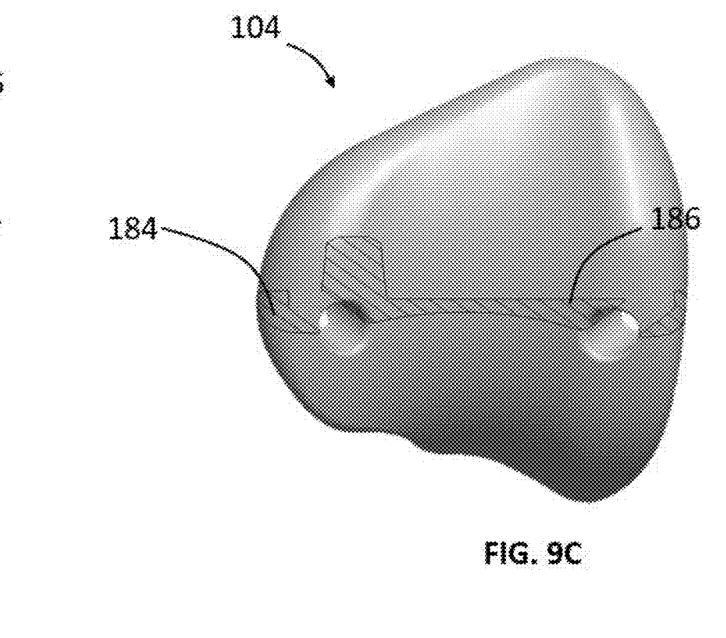

FIGS. 9A-9C shows the patellofemoral trial 104 in accordance with the preferred embodiment. The trial 104 has a proximal surface 188 in which the first and second apertures 184, 186 extend therethrough. The proximal surface 188 is the surface in which a patellofemoral groove 192 is located. The first and second apertures 184, 186 extend from the proximal surface 188 along a first aperture axis 180 and a second aperture axis 182 respectively. The first and second aperture axes 180, 182 define a second angle 183. The outer surfaces of the first and second apertures 184, 186 define a first sidewall 194 and a second sidewall 196. The first and second sidewalls 194, 196 extend along the first and second aperture axes 180, 182 respectively. A distal surface 198 of the trial 104 has at least a bone-engaging protrusion or pegs 190, and at least one of a multitude of pegs 190 are aligned in the same plane of the first and second aperture axes 180, 182. While apertures 184, 186 are shown in this embodiment, other embodiments can have various other engagement features to engage with the distal ends of the arms of the implant extractor. For example, the engagement features can include a hole, side wall, set back, or recess that engages with the arms of the implant extractor to attach same to the trial or implant.

Figure 10A:
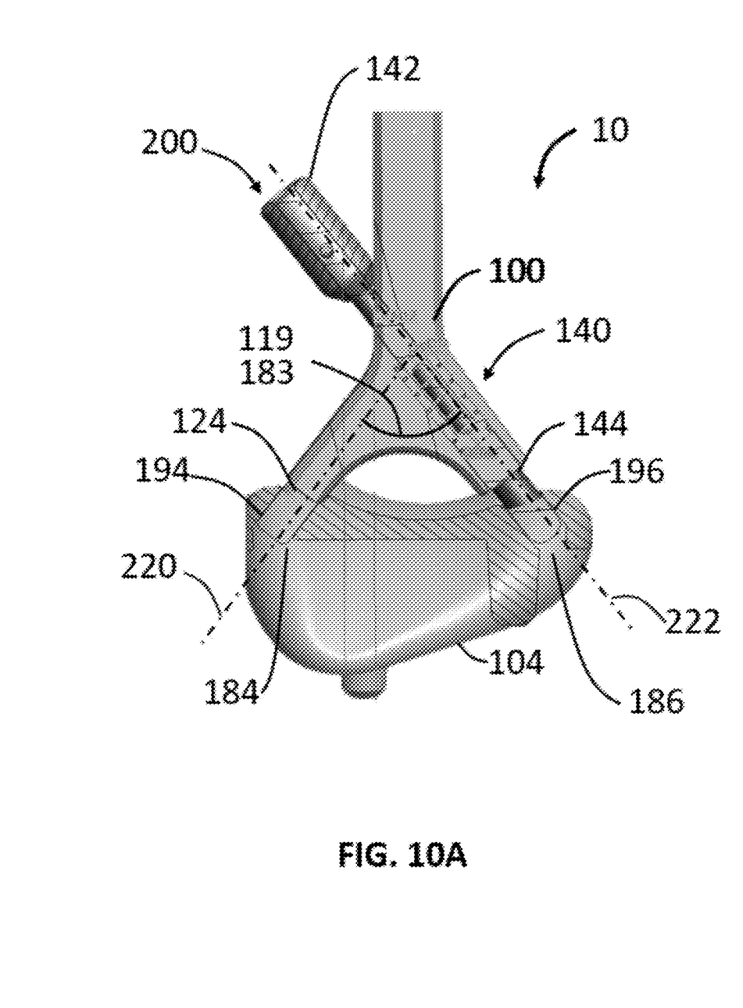
FIGS. 10A and 10B show a front and side prospective view of the implant extractor and the patellofemoral trial of FIG. 2A.
Figure 10B:
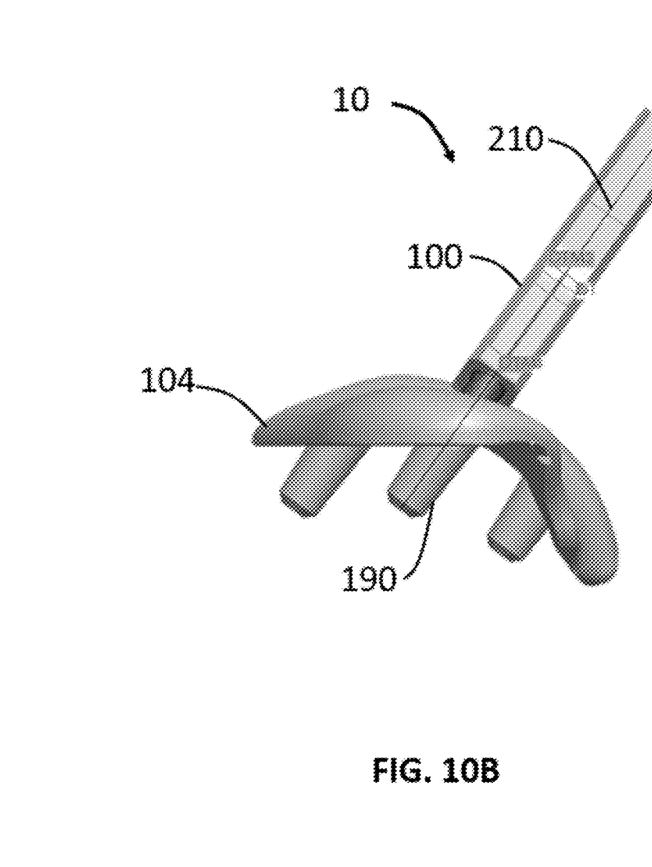
Figure 11A:
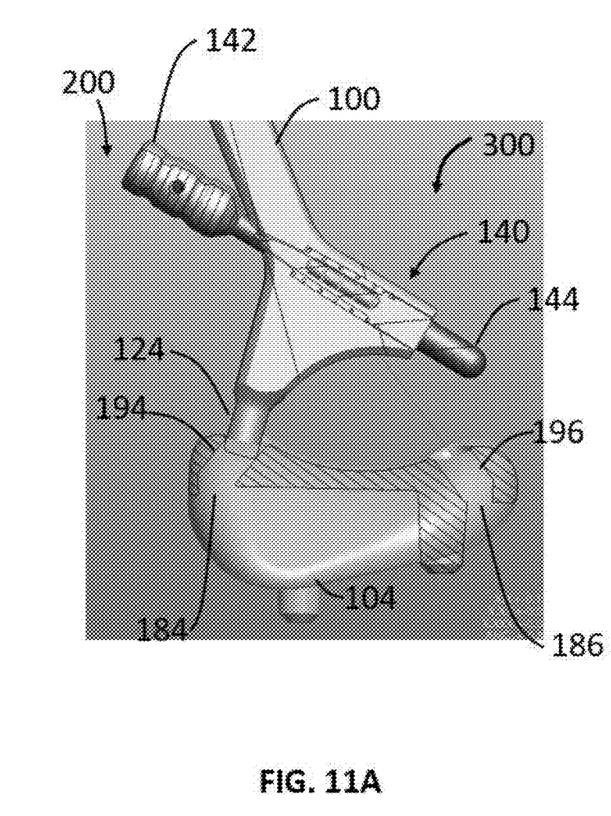
FIGS. 11A-11D show side perspective views of steps for engaging the implant extractor to the patellofemoral trial of FIG. 2 in accordance with another embodiment of the present disclosure.
Figure 11B:
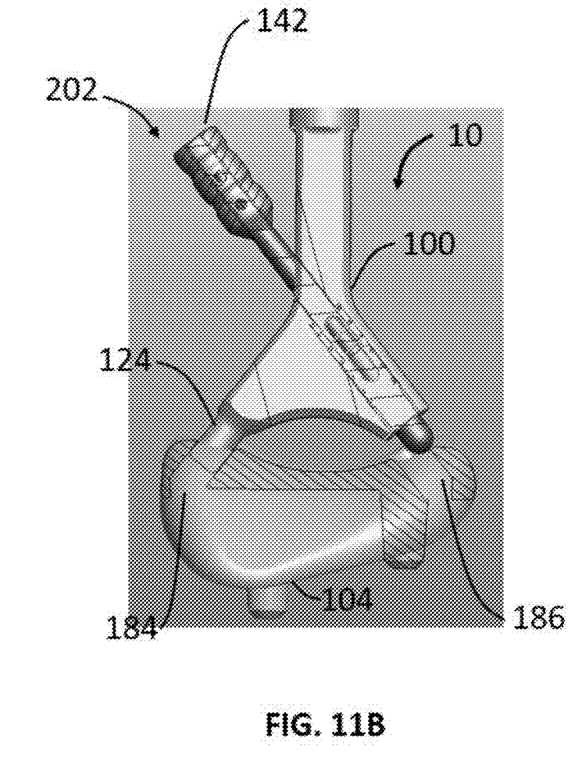
Figure 11C:
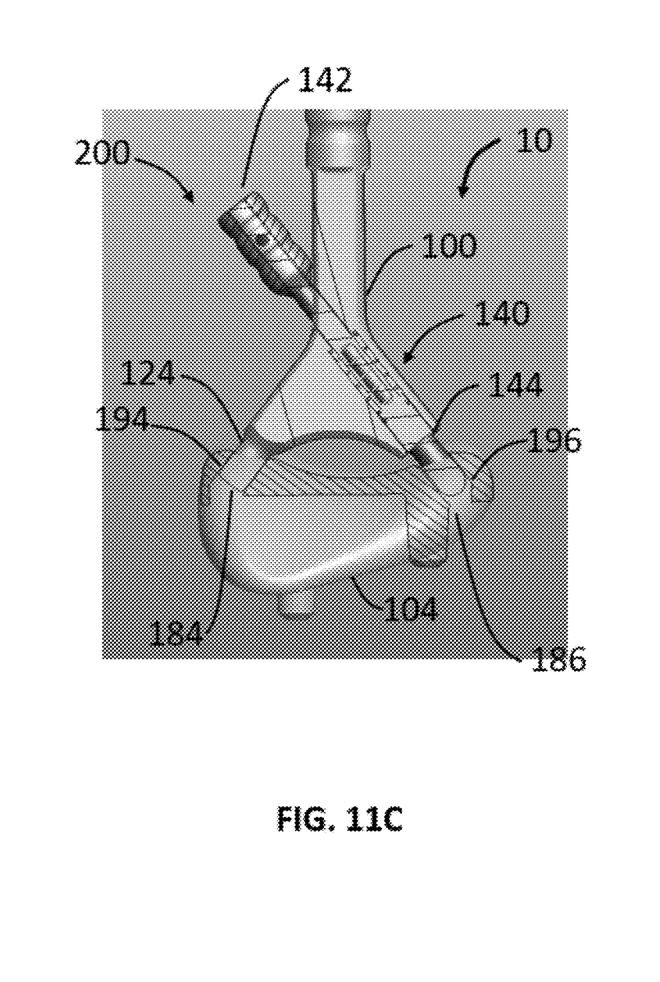
Figure 11D:
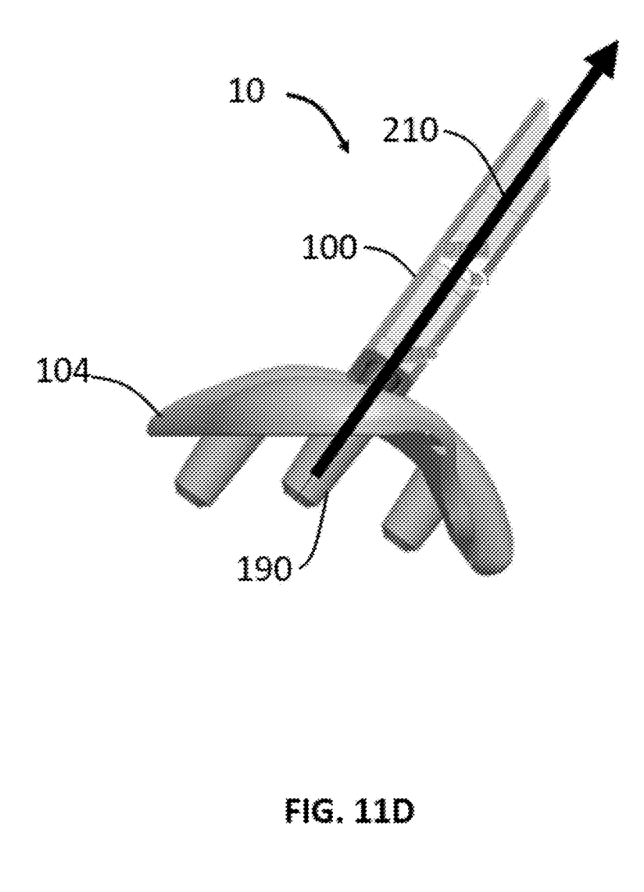

As shown in FIGS. 10A and 10B, by having the first angle 119 of the implant extractor 100 and the second angle 183 of the trial 104 equal, the first and second axes 116, 118 of the implant extractor 100 are alignable in the second position 200 with the first and second aperture axes 180, 182 of the trial 104. The aligned first axis 116 of the implant extractor 100 and the first aperture axis 180 of the trial 104 form a common first axis 220, and likewise, the aligned second axis 118 of the implant extractor 100 and the second aperture axis 182 of the trial 104 form a common second axis 222 such that the first and second distal ends 124, 144 are received in the first and second apertures 164, 186 respectively. Having the handle 142 movable boss in the second position 200, the first and second distal ends 124, 144 of the implant extractor 100 are urged against the first and second sidewalls 194, 196 respectively. In a preferred embodiment, the connection between the first and second arms 128, 130, and the first and second apertures 184, 186 is identical, and thus the arms 128, 130 and apertures 184, 186 are interchangeable for ease of use. This is preferably achieved by having the same diameter for the first and second distal ends 224, 144 and the same diameter for the first and second apertures 164, 186. The dimensions of the first and second apertures 184, 186 are greater than the dimensions of first and second distal ends 124, 144 to allow for a loose fit. It is preferable to have the first and second distal ends 124, 144 loosely fit into the first and second apertures 184, 186 in a non-rigid connection to allow for ease of insertion and manipulation The non-rigid connection allows for movement of the implant extractor 100 relative to the trial 104. The non-rigid connection helps to avoid transferring forces to the bone during extraction.

Referring now to FIGS. 11A-11D, there is shown a method for engaging the implant extractor 100 onto a patellofemoral trial 104 according to another embodiment of the present disclosure. In a first step 300, with the movable boss 140 in a second position 200, the first distal end 124 is inserted in the first aperture 184 of the trial 104. In a second step 310, the handle 142 is pulled in an outward direction such that the movable boss 140 is in the first position 202. With the movable boss 140 in the first position 202, the implant extractor 100 can be placed over the trial 104 such that the second distal end 144 of the movable boss 140 aligns with the second aperture 186 of the trial 104. In step 320, with the second end 144 of the movable boss 140 aligned with the second aperture 186 of the trial 104, the handle 142 can be released. Releasing the handle 142 in step 320 causes the biasing element 146, which is a spring 146, to urge the second distal end 144 of the movable boss 140 into the second position, urging the second distal end 144 into the second aperture 186. With the first and distal ends 124, 144 inserted in their respective first and second apertures 184, 186, the implant extractor 100 is fully engaged with the trial 104. A non-rigid connection is thus formed between the implant extractor 100 and the trial 104. Finally, in step 330, the user is able to pull the engaged implant extractor 100 in a distal to proximal direction along a common plane 210, removing the trial from the patient's bone. In another embodiment of the present method, the first and second distal ends 124. 144 may be interchangeably connected to the first and second apertures 184, 186. This minimal implant extractor 100 aids in keeping incision cites small, as cutting around the trial 104 is not required, merely enough clearance to engage the trial 104 and fully pull the trial 104 out.

Figure 12A:
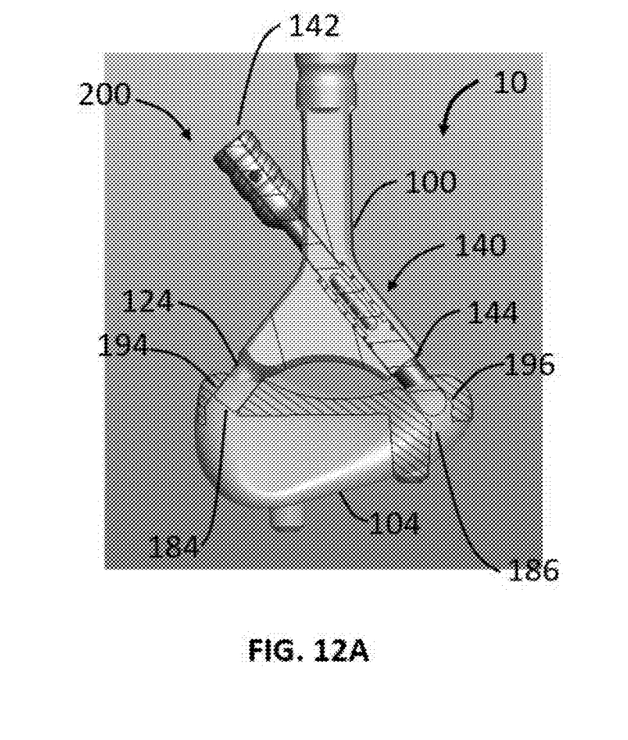
FIGS. 12A and 12B show side perspective views of steps for disengaging the implant extractor from the patellofemoral trial of FIG. 2 in accordance with another embodiment of the present disclosure.
Figure 12B:
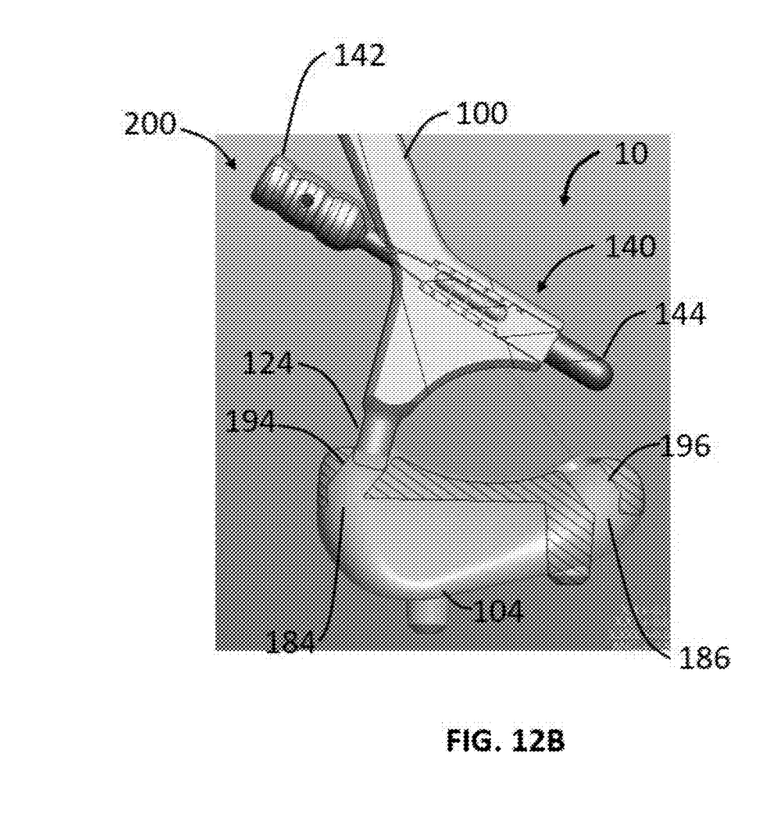

Referring now to FIGS. 12A-12B, there is shown a method for disengaging the implant extractor 100 from the patellofemoral trial 104 according to another embodiment of the present disclosure. In steps 380 and 390, the handle 142 of the movable boss 140 is pulled in an outward direction from the second position 200 to the first position 210 (not shown). With the movable boss in the first position 210, the second distal end 144 is retracted and the implant extractor 100 can be fully removed from the patellofemoral trial 104.

In another embodiment 400 of the present invention, the movable boss 140 and second distal end 144 may be a spring-loaded pin, which may be engaged with the second aperture 186 by pressing the entire body 110 of the implant extractor 110 onto the trial 104, the non-rigid connection between extractor 110 and trial 104 allows for the second distal end 144 to self-locate and automatically engage the second aperture 186 as the spring-loaded pin is released and decompresses.

In another embodiment 500 of the present invention, the movable boss 140 need not be a spring 146. The movable boss 140 may be a threaded rod inserted into a threaded channel, with the threaded rod being advanced along the second axis by turning the handle. The movable boss may also be a lockable latch without a biasing element. The lockable latch may have a first and second position in which the user slides the latch along the second axis securing the latch into the second position by way of common securing means.

In another embodiment 600 of the present invention, there may be a third arm along a third axis. The third arm may be movable. The angles between the first, second and third arms being less than 180 degrees in-between them.

In another embodiment 700, a slap-hammer mechanism, a leverage mechanism or an ultrasonic motor may be affixed to the body 112 allowing for greater trial or implant separation from the bone.

In another embodiment 800, the arms are configured to engage with a multitude of implants throughout the body, adjusting, for example, the angle between the arms, diameters of the distal ends, and lengths of the arms.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An orthopaedic instrument comprising:
   a body extending along a central axis; and
   first and second arms extending distally from a distal portion of the body along first and second axes respectively, the first and second axes being transverse to the central axis, the first and second arms having first and second distal ends respectively, the second distal end being moveable from a first position to a second position along the second axis, the distal ends configured to engage first and second engagement features of an implant, the first and second engagement features having first and second side walls respectively,
   wherein the first and second axes define a first angle therebetween such that when the first distal end is operatively coupled to a first engagement feature of the implant and the second distal end is in the second position, the second end is received in a second aperture of the implant such that the first and second distal ends are urged against the first and second side walls respectively to secure the instrument to the implant,
   wherein when the first distal end is received in the first engagement feature and the second distal end is in the first position, the instrument can be disengaged from the implant.

2. The instrument of claim 1, wherein the first and second distal ends have first and second dimensions respectively and the first and second engagement feature have first and second engagement feature dimensions respectively, the first and second engagement feature dimensions being greater than the first and second dimensions respectively such that a non-rigid connection is formed between the instrument and the implant when the instrument is secured to the implant to allow movement of the instrument relative to the implant.

3. The instrument of claim 1, wherein the second arm includes a biasing element to urge the second distal end to the second position.

4. The instrument of claim 3, wherein the second distal end is a moveable boss disposed in the second arm.

5. The instrument of claim 4, wherein a proximal end of the second arm includes a handle to pull the moveable boss from the second position to the first position.

6. The instrument of claim 5, wherein the biasing element is a spring disposed around the boss.

7. The instrument of claim 1, wherein a distal surface extending between the first and second arm is contoured.

8. The instrument of claim 1, wherein the body includes a grip to hold the instrument.

9. The instrument of claim 1, wherein the first angle is less than 180 degrees.

10. The instrument of claim 1, wherein the first and second engagement feature extend through first and second aperture axes respectively, the first and second engagement feature axes defining a second angle therebetween.

11. The instrument of claim 10, wherein the first angle and the second angle are equal.

12. The instrument of claim 1, wherein the first and second side walls extend along the first and second engagement feature axes respectively.

13. The instrument of claim 1, wherein the engagement features are any of a recess, aperture, side wall, setback and groove.

14. A orthopaedic system comprising:
   an instrument having a body extending along a central axis, first and second arms extending distally from a distal portion of the body along first and second axes respectively, the first and second axes being transverse to the central axis, the first and second arms having first and second distal ends respectively, the second distal end being moveable from a first position to a second position along the second axis;
   an implant having first and second apertures configured to receive the first and second distal ends respectively, the first and second engagement feature having first and second side walls respectively,
   wherein the first and second arms define a first angle, the first and second engagement feature define a second angle, the first and second angles being equal such that first and second ends are urged against the first and second side walls respectively to secure the instrument to the implant,
   wherein when the first distal end is received in the first engagement feature and the second distal end is in the first position, the instrument can be disengaged from the implant.

15. A method for engaging or disengaging an implant extractor to a first and a second engagement feature of the implant, the extractor having a body extending along a central axis, first and second arms extending distally from a distal portion of the body along first and second axes respectively, the first and second axes being transverse to the central axis, the first and second arms having first and second distal ends respectively, the second distal end being moveable from a first position to a second position along the second axis, the method comprising:
   engaging the first arm into one of the two engagement feature;
   pushing the body onto the implant such that the second arm is engaged with the second engagement feature, the second arm having a movable boss; and extracting the implant by pulling in a distal to proximal direction.

16. The method of claim 15, wherein a proximal end of the second arm includes a handle to pull the moveable boss from a second position to a first position.

17. The method of claim 16, wherein the second arm has a biasing element.

18. The method of claim 16, wherein the movable boss is disengaged by pulling the handle of the second arm in an outward direction from a first position to a second position, such that the second arm is removed from the second engagement feature.

19. The method of claim 18, wherein the implant extractor is pulled in an outward direction, such that the first arm and the second arm are removed from the first engagement feature and second engagement feature respectively.

* * * * *